United States Patent [19]

Konings et al.

[11] Patent Number: 5,371,162
[45] Date of Patent: Dec. 6, 1994

[54] STORAGE-STABLE SILICONE COMPOSITION

[75] Inventors: Mark S. Konings, Minneapolis; Jeff P. Tane, St. Paul, both of Minn.

[73] Assignee: Minnesota Mining and Manufacturing Company, St. Paul, Minn.

[21] Appl. No.: 911,151

[22] Filed: Jul. 9, 1992

[51] Int. Cl.$^5$ .............................................. C08G 77/08
[52] U.S. Cl. .................................. 528/15; 528/21; 528/31; 528/32; 525/478; 525/479; 524/714; 524/188; 524/251; 524/252
[58] Field of Search ................. 528/15, 21, 31, 32; 525/478, 479

[56] References Cited

U.S. PATENT DOCUMENTS

| | | | |
|---|---|---|---|
| 3,159,601 | 12/1964 | Ashby | 260/46.5 |
| 3,159,662 | 12/1964 | Ashby | 260/448.2 |
| 3,220,972 | 11/1965 | Lamoreaux | 260/46.5 |
| 3,410,886 | 11/1968 | Joy | 260/448.2 |
| 3,419,593 | 12/1968 | Willing | 528/15 |
| 3,715,334 | 2/1973 | Karstedt | 260/46.5 |
| 3,723,567 | 3/1973 | Mink et al. | 260/825 |
| 3,775,452 | 11/1973 | Karstedt | 260/429 R |
| 3,795,656 | 3/1974 | Martin | 260/46.5 E |
| 3,814,730 | 6/1974 | Karstedt | 260/46.5 |
| 4,045,390 | 8/1977 | Itoh et al. | 260/18 S |
| 4,239,867 | 12/1980 | Legrow et al. | 525/478 |
| 4,292,434 | 9/1981 | Lindner et al. | 556/479 |
| 4,398,010 | 8/1983 | Adkins | 528/15 |
| 4,670,531 | 6/1987 | Eckberg | 528/15 |
| 4,786,702 | 11/1988 | Sam et al. | 528/15 |
| 4,801,642 | 1/1989 | Janik et al. | 524/714 |
| 4,879,339 | 11/1989 | Yoshino et al. | 524/740 |

FOREIGN PATENT DOCUMENTS

| | | |
|---|---|---|
| 0416471 | 8/1990 | European Pat. Off. . |
| 0427183 | 5/1991 | European Pat. Off. . |
| 0427236 | 5/1991 | European Pat. Off. . |
| 2602781 | 2/1988 | France . |
| 3-95267 | 10/1989 | Japan . |
| 395267 | 4/1991 | Japan . |

OTHER PUBLICATIONS

S. Middleman, *Fundamentals of Polymer Processing*, 327–33, McGraw-Hill, N.Y.

*Primary Examiner*—John C. Bleutge
*Assistant Examiner*—Margaret W. Glass
*Attorney, Agent, or Firm*—Gary L. Griswold; Walter N. Kirn; F. Andrew Ubel

[57] ABSTRACT

The present invention provides shelf-stable RTV silicones which are useful for preparing sealants, caulks, adhesives, coatings, molding materials, lithographic plates, release liners and reflective sheets. The silicone composition of the present invention comprises: (a) a curable silicone polymer, e.g., vinyl-containing organopolysiloxane, (b) a crosslinker, e.g., organohydrogenpolysiloxane, (c) a platinum catalyst of the Karstedt type and (d) an amine stabilizer.

29 Claims, No Drawings

STORAGE-STABLE SILICONE COMPOSITION

TECHNICAL FIELD

This invention relates to curable high temperature storage-stable polysiloxane compositions, which compositions are useful for preparing sealants, caulks, adhesives, coatings and molding materials. This invention further relates to high temperature storage-stable polysiloxane compositions, which compositions are useful for preparing dental impressions and medical and dental implants.

BACKGROUND

"Silicones" are synthetic polymeric materials that possess an extraordinarily wide range of physical properties. They can be low- or high-viscosity liquids, solid resins, or vulcanizable gums. They display an unusual combination of organic and inorganic chemical properties that are due to their unique molecular structure of alternating silicon and oxygen atoms; this "polysiloxane" chemical structure is common to all silicones. Silicone polymers can be mixed with other chemicals and fillers into an enormous variety of products that serve in a multitude of applications. For a general discussion of silicone chemistry see "Silicones", *Kirk-Othmer Encyclopedia of Chemical Technology*, 3rd Ed., 20, 922–962(1982).

The fundamental component of a silicone composition is the polysiloxane referred to earlier and as depicted below in formula F1.

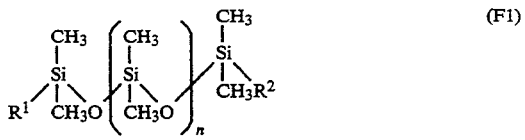

These polymers are made by an equilibrium process from other siloxanes and typically range in viscosity from about 0.01 Pa s to 2500 Pa s.

The room-temperature-vulcanizing ("RTV") silicones are a special class of silicones that have as a common attribute the development of a "crosslinked" elastomer from relatively low molecular weight linear polymers by means of a chemical reaction that forms these crosslinks and effectively extends chain length simultaneously. RTV silicones (e.g., addition cure silicones) have many applications in industry including use as sealants, caulks, adhesives, coatings, molding materials, dental impression materials and medical and dental implants.

An essential ingredient in an RTV silicone is a crosslinking component (hereinafter the "crosslinker") that reacts with the functional group or groups of the polymer chains (e.g., $R^1$ and $R^2$ of formula F1) to simultaneously lengthen them and connect them laterally to form the crosslinked network characteristic of a RTV silicone elastomer. Usually a catalytic agent is included to facilitate the reaction of the crosslinker with the polymer's functional groups.

There are many types of RTV silicones and likewise many types of crosslinking components and catalysts. Two such systems include (i) condensation cured silicones and (ii) addition cured, e.g., hydrosilylation cured (alternatively spelled "hydrosilation"), silicones. Condensation cured silicones characteristically, and in many instances detrimentally, release water (or alcohol) as a by-product of the crosslinking reaction. In contrast, there is no by-product in an addition cured silicone. The crosslinking reaction in these systems is typically triggered by combining the silicone polymer, the crosslinker and the catalyst. A variety of catalysts initiate and accelerate condensation curing such as amines and carboxylic acid salts of tin. At low temperatures the condensation cured silicone typically requires long times to fully cure (hours or even days). Higher catalyst concentrations and/or higher temperatures can shorten the cure time.

Unfortunately, condensation cured silicones typically suffer from an unacceptably large dimensional change upon curing or post curing. Applications which require precise dimensional accuracy (e.g., a dental impression) are adversely affected by these dimensional changes. When a condensation cured impression is used as a model for the formation of a dental crown or bridge the inaccuracy of the silicone is transferred to the dental crown or bridge. This results in a poorly fitting dental appliance which may cause pain or discomfort to the patient.

Addition cured silicones (e.g., hydrosilylation cured silicones) are generally considered to be of higher quality and are dimensionally more accurate than condensation cured silicones. Unlike condensation cured silicones, addition cured silicones do not produce detrimental by-products during curing. Addition cured silicones differ from condensation cured silicones in that the addition cured composition typically contains:

(1) a polymer which contains one or more vinyl functional groups,
(2) a crosslinker component containing one or more Si-H bonds, and
(3) a platinum catalyst.

A particularly preferred addition cured silicone is formed by reacting (1) a vinyl-containing organopolysiloxane with (2) an organohydrogenpolysiloxane. This reaction is typically facilitated by the presence of (3) a platinum catalyst of the Karstedt type. Platinum catalysts of the Karstedt type are described in U.S. Pat. Nos. 3,715,334, 3,775,452 and 3,814,730 which are herein incorporated by reference.

When RTV silicones are used as modeling compounds (e.g., dental impression materials) it is customary to provide the compound to the user as two separate mixtures (i.e., the catalyst is separately stored from the crosslinker). When the user is ready to prepare an impression or model she will mix the two parts together, place the silicone against the surface or object to be modeled and then wait until the silicone completely cures. The cured silicone is then removed from the surface or object and retains a negative impression of that surface. A positive model may then be formed by filling the impression cavity with a material such as gypsum or plaster of paris. In many instances it may not be feasible to form the positive model immediately. Therefore, it is also important that the impression retains its dimensional accuracy over a long period of time (often weeks or months).

The setting reaction of an RTV silicone is triggered, in general, by the mixing together of the catalyst, crosslinker and polymer. By varying the amount of catalyst and crosslinker, the rate of setting may be adjusted. As the material begins to set its viscosity increases. Eventually, the mixture becomes "gelled" and is irreversibly changed into a crosslinked polymer or an "elastomer."

At the gel-point the material no longer easily flows or adapts to new shapes. Therefore, in applications such as dental impressioning this period of time defines the extent of the "working time" period.

When the reaction is complete the material is said to be "set." This "setting time" is likewise an important parameter for a silicone impression material as it is crucial that the material remain against the surface it is to replicate until it has completely set. It is desirable to have a short setting time (e.g., less than 10 minutes). Premature removal from the surface being replicated may result in a distorted impression which will continue to crosslink, in the distorted position, outside of the mouth. Unfortunately, this situation is often initially unnoticed by the dentist and is discovered only after an expensive, but worthless, dental appliance has been fabricated. The dentist and patient must then go through the whole lengthy process again. This is a great expense and inconvenience.

The rate of setting may be further adjusted by the incorporation of well known inhibitors and/or retarders. One such inhibitor is 1,3,5,7-tetramethyl-1,3,5,7-tetravinylcyclotetrasiloxane. These retarders often operate by competitively reacting with the catalyst thereby slowing the crosslinking reaction. In general, with the slowing of the reaction both the working time and the setting time are affected.

For applications requiring detailed reproduction, such as dental impression materials, the setting time and the working time parameters are very important and must be carefully controlled. As previously mentioned, the working time measures the time period over which the mixed silicone material remains fluid enough to flow and change shape. After the reaction has reached the gel point the material's properties change drastically and resist further fluid flow. It is desirable to have sufficient working time so that the dentist may easily, and prior to crosslinking, (1) mix the materials and (2) place them in the mouth.

One major factor which affects both the working time and the setting time is the catalyst activity. Unfortunately, platinum catalysts of the Karsted variety are somewhat sensitive to degradation and therefore are of variable activity. While the exact mechanism is presently unknown, this degradation may be advanced at high temperatures (such as might be encountered in a hot warehouse or in a truck-trailer). Over time the catalyst composition is believed to degrade and the setting time of the mixed composition becomes longer and longer. As previously mentioned even small changes in the setting time can have a detrimental affect on the accuracy of an impression if the user removes the material prior to its complete cure. Such early removal becomes more likely if the catalyst activity unexpectedly decreases upon storage. In extreme cases the silicone composition may never completely set due to this degradation effect. It would therefore be desirable to have a high-temperature storage-stable RTV silicone material which resists degradation at elevated temperatures.

SUMMARY OF THE INVENTION

The present invention relates to RTV silicone compositions that possess greatly extended shelf life when stored at elevated temperatures. These compositions are prepared using amine stabilizers. These amines in particular stabilize platinum catalysts of the Karstedt variety used in the silicone composition. Advantageously, these stabilizers do not adversely affect the initial room temperature setting properties of the RTV silicone material.

The present invention provides, in another aspect, shelf-stable dental impression materials which comprise hydrosilylation cured silicones comprising amine stabilizers and Karstedt catalysts. Most preferred are two-part addition cure compositions. The invention also provides methods for preparing and methods for using such impression systems.

The present invention provides, in another aspect, shelf-stable RTV silicones which are useful for preparing sealants, caulks, adhesives, coatings, molding materials, lithographic plates, release liners and reflective sheets.

The silicone compositions of the present invention comprise:
 (a) curable silicone polymer, e.g., vinyl-containing organopolysiloxane,
 (b) crosslinker, e.g., organohydrogenpolysiloxane,
 (c) platinum catalyst of the Karstedt type and
 (d) stabilizer, e.g., amine stabilizer.

Presently preferred optional ingredients of the silicone composition include fillers (e.g., pulverized metals, silica, quartz, calcium carbonate or metal oxides), appropriate polymerization initiators and inhibitors, pigments, surfactants, modifying agents, and copolymerizable and non-copolymerizable cosolvents, and the like.

The silicone of the present invention can be prepared by combining (e.g., mixing) the vinyl-containing organopolysiloxane, the organohydrogenpolysiloxane, the platinum catalyst and the amine stabilizer. Prior to use the components are pre-mixed into preferably two parts. For example, part "A" may contain the vinyl-containing organopolysiloxane, the platinum catalyst and the amine stabilizer, while part "B" may contain the organohydrogenpolysiloxane and optionally vinyl-containing organopolysiloxane.

The pre-mixed part "A" has been found to possess increased shelf stability when exposed to elevated temperatures. As a result, the subsequent mixing of parts "A" and "B" provides silicone compositions which have more reproducible working times and setting times. This feature is particularly beneficial in uses such as dental impressioning as the dentist is less likely to prematurely remove the impression material from the mouth thereby causing a distorted impression.

DETAILED DESCRIPTION OF THE PRESENTLY PREFERRED EMBODIMENTS

The term "Silicone", as used herein, refers to a polymer having alternating silicon and oxygen atoms (i.e., a polysiloxane chemical structure) and having sufficient pendant functional groups to undergo a setting reaction in the presence of a crosslinker compound and a catalyst compound.

The term "RTV", as used herein, refers to silicones that have as a common attribute the development of a crosslinked elastomer from relatively low molecular weight linear or branched polymers by means of a chemical reaction that forms these crosslinks and effectively extends chain length simultaneously at room temperature.

"Room temperature" vulcanizing implies that the curing reaction proceeds at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods.

The term "crosslinked polymer", as used herein, refers to polymers that react with the functional group or groups of the polymer chains (i.e., $R^1$ and $R^2$ of figure F1) to simultaneously lengthen them and connect them laterally to form the crosslinked network characteristic of a RTV silicone elastomer. In contrast to a thermoplastic polymer (i.e., a polymer that softens and flows upon heating) a crosslinked polymer, after crosslinking, is characteristically incapable of further flow.

The term "working time", as used herein, refers to the time between the beginning of the setting reaction, i.e., when the vinyl-containing organopolysiloxane, the organohydrogenpolysiloxane, and the platinum catalyst are mixed and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to comfortably mix and place the composition into its desired form. For dental impression compositions the working time is preferably greater than 0.5 minutes, more preferably greater than 2 minutes and most preferably greater than 5 minutes. Longer working times are also acceptable.

The term "setting time", as used herein, refers to the time sufficient curing has occurred to allow removal of the silicone material from the surface being replicated without causing permanent deformation of said silicone material. The setting time may be approximated, for example, by measuring the torque of the reacting composition on a oscillatory rheometer. When the torque value reaches a maximum value the material is said to be fully set. An arbitrary torque value which is less than the typical maximum value may alternatively be used as a relative approximation of the set time. In general, shorter setting times are preferred over longer setting times. Preferably the setting time is less than 10 minutes. More preferably the setting time is less than the sum of 5 minutes plus the working time. Most preferably the setting time is just longer than the desired working time.

(a) Curable silicone prepolymer

In the practice of the present invention, the curable silicone composition can be a multiple-component composition cured by the presence of crosslinking agents and catalysts. Most preferred are two-part addition cure compositions of the room temperature vulcanizing ("RTV") variety. The composition contains a "curable silicone prepolymer", that is, a polysiloxane having one or more functional groups, e.g., vinyl groups, which enable the prepolymer to be polymerized or cured to a state of higher molecular weight. Suitable silicone prepolymers are well-known in the art and are described, for example, in "Silicones", *Kirk-Othmer Encyclopedia of Chemical Technology*, 3rd Ed., 20, 922–962 (1982).

The fundamental component of a silicone compositions is the polysiloxane referred to earlier and as depicted in formula F1.

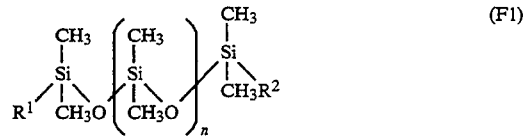

These polymers are made by an equilibrium process from other siloxanes and typically range in viscosity from about 0.01 Pa s to 2500 Pa s. The preferred molecular weight of the polysiloxane often depends upon the desired viscosity of the composition prior to crosslinking. In general, as the molecular weight is increased the viscosity of the uncrosslinked composition correspondingly increases. For uses as molding compositions, the average value of n is preferably between 10 and 6000. More preferably the average value of n is between 50 and 2000, and most preferably the average value of n is between 100 and 1000. Mixtures of more than one molecular weight may likewise be utilized.

The groups $R^1$ and $R^2$ of formula (F1) represent the "terminal" portions of the polymer chain and are often the sites for the attachment of said one or more functional groups, i.e., the groups which participate in the crosslinking reaction. It is also contemplated that one or more sites depicted in formula (F1) as having methyl groups could instead contain the one or more functional groups. Likewise, $R^1$ and/or $R^2$ may not be the site of the one or more functional groups. Therefore, formula (F1) is intended to merely represent a "typical" polysiloxane polymer with terminal functional groups. The site of attachment of the functional groups is not presently believed to be particularly important.

The one or more functional groups are in general unsaturated aliphatic groups having 1 to 20 carbon atoms, such as alkenyl or cycloalkenyl, e.g., vinyl, allyl, 1-hexenyl and cyclohexenyl. A preferred unsaturated aliphatic group is vinyl.

When special properties are needed, other monovalent hydrocarbyl and halogenated monovalent hydrocarbyl groups (e.g., alkyls, phenyl, cyanoethyl, and trifluoropropyl) can be substituted for the methyl groups of formula (F1).

The preferred amount of the polysiloxane component will vary depending upon the desired physical properties of the silicone composition (such as the desired uncured viscosity, cured hardness, etc.). In part due to the wide range of acceptable molecular weights for the polymer component and the many types of adjuvants which may be added to the polymer this amount will vary widely. The presently preferred amount of polymer component is between 10% and 100% by weight. More preferably the polymer component is between 20% and 90% by weight. Most preferably the polymer component is between 20% and 80% by weight.

(b) Crosslinker

The crosslinker component (e.g., organohydrogenpolysiloxane) contains at least one silicon-hydrogen linkage and can be a polymeric compound or a compound that is not polymeric. These compounds are well known in the art and are disclosed, for example in U.S. Pat. Nos. 3,159,662 to Ashby; 3,220,972 to Lamoreaux; and 3,410,886 to Joy. The crosslinker containing the silicon-hydrogen linkage should contain at least two silicon-hydrogen linkages per molecule, with no more than three hydrogen atoms attached to any one silicon atom.

Some classes of compounds having a silicon-bonded hydrogen atom which can be used in the invention are:

(a) organohydrogensilanes having the empirical formula,

$$(H)_a(R^3)_b Si_c \quad (F2)$$

wherein each $R^3$ can be the same or different and represents an organic group, preferably selected from the group consisting of monovalent hydrocarbyl groups, monovalent hydroalkoxyl groups and halogenated monovalent hydrocarbyl groups, c represents an integer having a value from 1 to 10,000, a represents an integer having a value at least 2 and less than or equal to c when c is greater than 1, and the sum of a and b equals the sum of 2 and two times c;

(b) organohydrogencyclopolysiloxanes having the empirical formula,

$$H_d R^3_e (SiO)_f \quad (F3)$$

wherein $R^3$ is as defined above, f represents an integer having a value from 3 to 18, d represents an integer having a value at least 2 and less than or equal to f, and the sum of d and e equals two times f; and (c) organohydrogenpolysiloxane polymers or copolymers having the empirical formula,

$$(H)_g(R^3)_h Si_j O_{(j-1)} \quad (F4)$$

wherein $R^3$ is as defined above, j represents an integer having a value from 2 to 10,000, g represents an integer having a value at least 2 and less than or equal to j, and the sum of g and h equals the sum of 2 and two times j.

Among the groups represented by $R^3$ include, for example, alkyl groups having 1 to 18 carbon atoms, e.g., methyl, ethyl, propyl, octyl, and octadecyl, cycloalkyl groups having 5 to 7 ring carbon atoms, e.g., cyclohexyl and cycloheptyl, aryl groups having 6 to 18 carbon atoms, e.g., phenyl, naphthyl, tolyl, xylyl, alkoxyl groups having 0 to 18 carbon atoms, e.g., hydroxyl, methoxyl, ethoxyl, propoxyl, and combinations of alkyl and aryl groups, e.g., aralkyl groups, such as, benzyl and phenylethyl, and halo-substituted groups thereof, e.g., chloromethyl, chlorophenyl, and dibromophenyl. Preferably, the $R^3$ group is methyl or both methyl and phenyl. The $R^3$ group can also be an unsaturated aliphatic group having 1 to 20 carbon atoms, such as alkenyl or cycloalkenyl, e.g., vinyl, allyl and cyclohexenyl. When the $R^3$ group is a group with aliphatic unsaturation, the silicon compound containing silicon-hydrogen linkages can be reacted with itself to form a polymer.

A preferred compound having silicon-bonded hydrogen useful in this invention is a polyorganohydrogenpolysiloxane having the general formula:

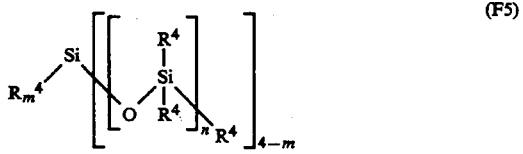
(F5)

wherein each $R^4$ can be the same or different and represents hydrogen, an alkyl group having 1 to 18 carbon atoms, a cycloalkyl group having 3 to 12 carbon atoms, or a phenyl group, at least two but not more than one-half of all the $R^4$ groups in the siloxane being hydrogen, m represents 0,1,2, or 3, and n represents a number having an average value from 1 to about 10,000.

The amount of the crosslinker component should be sufficient to provide the desired degree of crosslinking of the silicone composition. In part due to the wide range of acceptable molecular weights for the polymer component, it is presently believed that this amount is best described in terms of the ratio of Si—H groups to functional groups in the composition. The presently preferred ratio of Si—H groups to functional groups ("SiH:V") is between 0.2:1 and 20:1. More preferably the SiH:V ratio is between 1:1 and 10:1. Most preferably the SiH:V ratio is between 1.5:1 and 4:1.

(c) Platinum catalyst of the Karstedt type

"Karstedt" platinum catalysts are described in U.S. Pat. Nos. 3,715,334, 3,775,452 and 3,814,730 which are herein incorporated by reference. In general, to produce a Karstedt catalyst, there must be utilized (A) platinum halide, and (B) a complexing material in the form of an unsaturated organosilicon material selected from:

(a) unsaturated silanes having the empirical formula,

$$R_a R'_b Si_c X_z, \quad (F6)$$

where R is free of aliphatic unsaturation and selected from monovalent hydrocarbon radicals, R' is selected from monovalent aliphatically unsaturated hydrocarbon radicals, X is a hydrolyzable radical, c is an integer having a value of between 1 and 10,000, b is an integer having a value greater than 2 and the sum of a, b and z equals the sum of 2 and two times c for a linear or branched silane and wherein c is an integer having a value from 4 to 18 and the sum of a, b and z equals two times c for a cyclic silane;

(b) unsaturated linear or branched siloxanes of the formula,

$$R_d R'_e Si_f O_{(f-1)}, \quad (F7)$$

where R and R' are as defined above, f is an integer having a value of between 2 and 10,000, e is an integer having a value greater than 2 and the sum of d and e equals the sum of 2 and two times f; and (c) unsaturated cyclic siloxanes of the formula,

$$R_d R'_e Si_f O_f, \quad (F8)$$

where R and R' are as defined above, f is an integer having a value from 3 to 18, and the sum of d and e equals two times f.

A Karstedt catalyst can be made by (1) effecting contact between an unsaturated organosilicon material as defined by formula (F6), (F7) or (F8) above, and a platinum halide to provide for the production of a mixture having a concentration of available inorganic halogen, (2) treating the resulting mixture of (1) to effect the removal of available inorganic halogen, and (3) recovering from (2), a platinum-siloxane complex having available inorganic halogen of less than 0.1 gram atoms of halogen, per gram atom of platinum, and preferably that the complex be substantially halogen free.

As used herein, the term "available inorganic halogen," will designate halogen that can be detected by a modification of ASTM designation D-1821-63 for "Inorganic Chloride." The procedure is substantially as described, except there is utilized in place of acetone a mixture of glacial acetic acid and acetone. The procedure employed for determining gram atoms of platinum in the platinum-siloxane complexes was Atomic Absorption Spectroscopy. For example, the method of R. Dockyer and G. F. Hames, Analyst, 84, 385 (1959).

Radicals included by R are, for example, alkyl radicals such as methyl, ethyl, propyl, butyl, hexyl, heptyl, octyl, etc.; cycloalkyl radicals such as cyclohexyl, cycloheptyl, etc.; aryl radicals such as phenyl, methyl, tolyl, xylyl, etc.; aralkyl radicals such as benzyl, phenylethyl, phenylpropyl, etc. Radicals included by R' are, for example, aliphatically unsaturated radicals such as ethynyl, 1-propynl, etc.; vinyl, allyl, and cycloalkenyl radicals, such as cyclopentenyl, cyclohexenyl, cycloheptenyl, cyclooctenyl, etc.

It is desirable that neither the R nor the R' radicals have chemically combined halogen since the presence of such halogen attached to the hydrocarbon group in the platinum complex will act to inhibit the catalysis effected by the complex. Accordingly, it is preferred to catalyze silanes and siloxanes of formulas (F6), (F7) and (F8) in forming the platinum catalyst of the present invention that do not have combined halogen.

Unsaturated silanes included by formula (F6) are, for example, tetravinylsilane, tri-allylmethylsilane, divinyldimethylsilane, tri-vinylphenylsilane, divinylmethylphenylsilane, divinylmethylethoxysilane, divinylmethylacetoxysilane, etc.

Included by the unsaturated siloxanes of formula (F7) are, for example, disiloxanes of the formula,

$$R_g R'_h SiOSiR'_h R_g, \quad (F9)$$

where R, R', are as defined above, h is an integer with a value per silicon atom of at least one and the sum of g and h, per silicon atom, is equal to 3. For example, there are included by disiloxanes of formula (F9), symdivinyltetramethyldisiloxane, 1,3-divinyltetramethyldisiloxane, hexavinyldisiloxane, 1,1,3-trivinyltriethyldisiloxane, symtetravinyldimethyldisiloxane, etc.

There are also included by the unsaturated siloxanes of formula (F8), cyclopolysiloxanes. For example, there is included 1,3,5-trivinyl-1,3,5-trimethylcyclotrisiloxane, 1,3,5,7-tetraallyl-1,3,5,7-tetraphenylcyclotetrasiloxane 1,3-divinyloctamethylcyclopentasiloxane, etc.

Preferably the above-described platinum-siloxane complexes of platinum and organosiloxanes of formula (F7) and (F8), can be made in accordance with the practice of the invention, as previously described, utilizing a platinum halide, and an unsaturated linear, branched or cyclic siloxane of formula (F7) or (F8) having at least one structural unit of the formula,

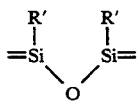

(F10)

where the unsatisfied valences of the above structural unit can be satisfied by R, R' and oxygen radicals and where R and R' are as previously defined.

The platinum halides which can be employed in the practice of the invention are, for example, $H_2PtCl_6.nH_2O$ and metal salts such as $NaHPtCl_6.nH_2O$, $KHPtCl_6.nH_2O$, $Na_2PtCl_6.nH_2O$, $K_2PtCl_6.nH_2O$.

Also, $PtCl_4.nH_2O$ and platinous type halides such as $PtCl_2, Na_2PtCl_4.nH_2O$, $H_2PtCl_4.nH_2O$, $NaHPtCl_4.nH_2O$, $KHPtCl_4.nH_2O$, $K_2PtBr_4$.

In addition, platinum halide complexes with aliphatic hydrocarbon as taught in Ashby U.S. Pat. Nos. 3,159,601 and 3,159,662, for example $[(CH_2=CH_2).PtCl_2]_2$; $(PtCl_2.C_3H_6)_2$, etc. Other platinum halides which can be utilized are shown by Lamoreaux U.S. Pat. No. 3,220,972, such as the reaction product of chloroplatinic acid hexahydrate and octyl alcohol, etc.

The amount of the platinum complex component should be sufficient to provide the desired degree of crosslinking of the silicone composition within a reasonable time. In part due to the wide range of acceptable molecular weights for the polymer component, it is presently believed that this amount is best described in terms of the ratio of Pt atoms to functional groups in the composition. The presently preferred ratio of Pt atoms to functional groups (37 Pt:V") is between 1:2 and 1:500. More preferably the Pt:V ratio is between 1:10 and 1:200. Most preferably the Pt:V ratio is between 1:30 and 1:70.

(d) Stabilizer

Suitable amines include compounds having the structure

(F11)

where N is nitrogen and the units R, which may be the same or different, are hydrogen atoms, hydrocarbyl groups, substituted hydrocarbyl groups, hydrocarbyl groups optionally interrupted with a heteroatom, alkoxyl groups, or groups in which two units R together with the element N form a cyclic ring system. The amine may be primary, secondary or tertiary, that is, in structure (F11) two, one or none of the units R respectively may be hydrogen atoms.

One or more of the groups R may be hydrocarbyl. The hydrocarbyl group may be, for example, alkyl, cycloalkyl, alkaryl or aryl. Suitably, the group R may be an alkyl group having from 1 to 10 carbon atoms.

Examples of suitable amines in which one or more of the units R is hydrocarbyl include propylamine, butylamine, pentylamine, hexylamine, dimethylamine, diethylamine, dipropylamine, di-n-butylamine, dipentylamine, trimethylamine, triethylamine, tripropylamine, tri-n-butylamine, tripentylamine. Examples of amines containing aromatic groups include N-methyl diphenylamine. An example of an amine containing alkoxyl groups is triethanolamine.

One or more of the units R may be a substituted hydrocarbyl group and in particular the hydrocarbyl group may carry a substituent having the structure

(F12)

where N is nitrogen and the unit $R^5$ is, for example, an alkylene chain and the units $R^6$, which may be the same or different, are for example, hydrogen atoms, hydrocarbyl groups or alkoxyl groups.

Examples of amines having the structure of formula (F11) in which at least one of the units R is a substituted hydrocarbyl group include: (i) diamines of the structure,

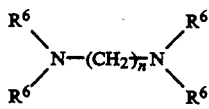 (F13)

wherein n is a whole number of at least two and the groups $R^6$, which may be the same or different, are hydrogen atoms, hydrocarbyl groups and especially alkyl groups; (ii) triamines; and (iii) tetraamines. For example, the amine may be ethylene diamine, trimethylene diamine, tetramethylene diamine, pentamethylene diamine or hexamethylene diamine, or N-hydrocarbyl, especially N-alkyl derivatives thereof. The amine may also be a triamine (e.g., diethylenetriamine, spermidine and alkylated derivatives thereof) or a tetraamine (e.g., triethylenetetraamine, spermine and alkylated derivatives thereof).

Examples of amines in which the element N forms part of a cyclic ring system include piperidine and N-hydrocarbyl, especially N-alkyl derivatives of piperidine.

Alternatively, one or more or the groups R may contain silicon or organopolysiloxane groups. Suitable amines include compounds of the structure

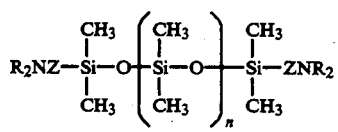 (F14)

where n preferably is an integer from 0 to 10,000, and Z is preferably an alkylene group independently having from 1 to 10 carbon atoms. More preferably n is an integer from 10 to 200 and Z has from 2 to 4 carbon atoms. Most preferably n is an integer from 10 to 200 and Z has three carbon atoms.

In general, amines which are soluble or miscible in the silicone composition are preferred over insoluble or immiscible amines. If desired, solubility or miscibility may be enhanced or achieved by incorporation of suitable cosolvents or dispersibilizing agents. It is presently believed that insoluble or immiscible amines may also be utilized in the present invention.

In certain applications the volatility of the amine component is of particular importance. Highly volatile amines, in general, exhibit a characteristic odor which may be objectionable for applications such as dental impression materials. In addition these amines are susceptible to evaporation from the silicone composition and are thereby rendered less effective as a long-term stabilizer. For example, trimethylamine is a gaseous amine and readily escapes from an open container of silicone composition. In the absence of a tightly sealed container it is expected that this amine would evaporate from the composition and thereby not be available to perform its role as a stabilizer for the platinum catalyst. Likewise, it would be difficult to manufacture (i.e., formulate or mix) such a silicone composition while avoiding loss of the volatile component (e.g., trimethylamine). In general, nonvolatile amines are less odorous and less likely to evaporate from the composition and are presently preferred.

The amount of the amine component should be sufficient to provide the desired degree of high-temperature stabilization of the platinum catalyst component. Preferably the amine component should provide sufficient stability to the composition such that the composition's set time remains substantially unaffected by exposure to high temperatures for prolonged periods, i.e., the set time after aging is preferably less than two times the initial set time. More preferably the composition's set time should remain substantially unaffected by exposure to 50° C. temperatures for periods of up to 10 days. Most preferably the composition's set time should remain substantially unaffected by exposure to 65° C. temperatures for periods of up to 20 days or longer. It is contemplated that the amine component will also provide increased storage stability when the composition is stored for prolonged periods at room temperature.

In part due to the wide range of acceptable molecular weights for the amine component, it is presently believed that the amount of amine component is best described in terms of the ratio of nitrogen atoms to platinum atoms in the composition. The presently preferred ratio of nitrogen to platinum ("N:Pt") is greater than 0.05:1. More preferably the N:Pt ratio is between 0.2:1 and 10:1. Most preferably the N:Pt ratio is between 0.8:1 and 4:1.

The present invention will be further understood in view of the following examples which are merely illustrative and not meant to limit the scope of the invention. Unless otherwise indicated, all parts and percentages are by weight.

PREPARATORY EXAMPLE 1

Preparation of a Karstedt catalyst

A three neck flask was fitted with a mechanical stirrer, reflux condenser, thermometer, and nitrogen purge and placed in a water bath. The flask was charged with 3,000 parts ethanol and 1,200 parts 1,1,3,3-tetramethyl 1,3-divinyl disiloxane and then purged with nitrogen for 5 minutes. Six hundred parts hexachloroplatinic acid was added to the solution and the mixture stirred until the acid was substantially dissolved. Eighteen hundred parts sodium bicarbonate was then added over a 5 minute period. The water bath was heated to 60° C. and then stirred for 2.5 hours. After cooling, the solution was filtered, washed with 150 parts ethanol and transferred to a flask containing 6,000 parts dimethylvinylsiloxy terminated polydimethylsiloxane. The flask was placed on a rotary evaporator and stripped at 45° C. until the vacuum reaches 0.5-1.0 mm Hg to produce a Karstedt type catalyst solution with a platinum concentration of approximately 2.3-3.0%.

PREPARATORY EXAMPLES 2-7

Stock catalyst compositions and stock crosslinker compositions were prepared by combining the following ingredients as listed in Table P1:

TABLE P1

| Ingredients | Preparatory Ex.: | | | | | |
|---|---|---|---|---|---|---|
| | 2 | 3 | 4 | 5 | 6 | 7 |
| HMW polysiloxane[1] | 4,600 | 3,000 | 4,600 | 3,000 | 3,200 | 1,400 |
| LMW polysiloxane[2] | 1,800 | 1,300 | 1,800 | 1,300 | 1,400 | 620 |
| platinum catalysts[3] | 100 | — | 100 | — | 69 | — |
| crosslinker[4] | — | 210 | — | 210 | — | 100 |
| cyclics[5] | — | 1.0 | — | 1.0 | — | — |
| microcrystalline silica[6] | — | — | 12,000 | 8,500 | — | — |
| calcium carbonate | — | — | 12,000 | 8,500 | — | — |
| TMDVDS[7] | — | — | — | — | 1.0 | — |
| mineral oil[8] | — | — | 2,200 | 1,500 | — | — |

TABLE P1-continued

| Ingredients | Preparatory Ex.: | | | | | |
|---|---|---|---|---|---|---|
| | 2 | 3 | 4 | 5 | 6 | 7 |
| pigment[9] | — | — | — | 150 | — | — |

[1]"HMW polysiloxane" = vinyldimethylsiloxy terminated polydimethylsiloxane with a viscosity of approx. 60 Pa s.
[2]"LMW polysiloxane" = vinyldimethylsiloxy terminated polydimethylsiloxane with a viscosity of approx. 2 Pa s.
[3]"platinum catalyst" = the platinum catalyst solution of Preparatory Example 1.
[4]"crosslinker" = organohydrogenpolysiloxane having a viscosity of approximately 24 to 38 mPa s and approximately 0.4% hydride.
[5]"cyclics" = 1,3,5,7-tetramethyl-1,3,5,7-tetravinylcyclotetrasiloxane.
[6]The addition of filler to Preparatory Examples 4 and 5 caused these compositions to become viscous putties rather than lower viscosity liquids.
[7]"TMDVDS" = 1,1,3,3-tetramethyl-1,3-divinyldisiloxane.
[8]"mineral oil" = USP grade mineral oil.
[9]"pigment" = V1107 Brown silicone paste available from Ferro Corp. Cleveland Ohio.

EXAMPLES 1-5

To 250 parts of the catalyst composition of Preparatory Example 2 were added varying amounts of amine as indicated in Table 1. The amine and the catalyst composition of Preparatory Example 2 were mixed until homogeneous. As a comparison, Example A represents the catalyst composition of Preparatory Example 2 without added amine.

TABLE 1

| Example | Additive | (parts) | N:Pt ratio |
|---|---|---|---|
| A | None | 0.00 | 0.00 |
| 1 | Triethylamine | 0.0028 | 0.05 |
| 2 | Triethylamine | 0.0085 | 0.15 |
| 3 | Triethylamine | 0.013 | 0.22 |
| 4 | Triethylamine | 0.058 | 1.10 |
| 5 | Trimethylethylenediamine | 0.0043 | 0.15 |

Equal volumes of the amine containing catalyst composition and the crosslinker composition of Preparatory Example 3 were placed in separate barrels of a two-part syringe (i.e., a syringe with two parallel barrels of essentially equal diameter) equipped with a Kenics static mixer. A Kenics static mixer consists of a circular pipe within which are fixed a series of short helical elements of alternating left- and right-hand pitch. The helical design of the central element causes a transverse flow to arise in the plane normal to the pipe axis. As a consequence, radial mixing of the two compositions is achieved. A complete description of the fluid mechanics of a Kenics static mixer may be found on pages 327 and 328 of *Fundamentals of Polymer Processing*, by Stanley Middleman.

The silicone compound begins to react (i.e., crosslink) upon mixing the two compositions together. Analysis of the setting time of the compositions was performed using a Monsanto Model 100 Oscillating Disc Rheometer. The setting time is determined by placing a mixed mass of material between the plates of the rheometer while measuring the torque (using 5 degree oscillation and 27° C. testing temperature). When the torque reaches 0.57 N m the material is said to have set.

Listed below in Table 2 are the results of the "initial" setting time measurement for each sample (i.e., the setting time measured on a freshly prepared sample) and the setting time obtained after "aging" the sample at 65° C. for 285 to 1075 hours.

TABLE 2

| Example | Additive | Aging Time (hours) | Setting Time Initial (secs.) | Setting Time Aged (secs.) |
|---|---|---|---|---|
| A | None | 285 | 125 | >800 |
| 1 | Triethylamine | 285 | 154 | 364 |
| 2 | Triethylamine | 454 | 124 | 123 |
| 3 | Triethylamine | 578 | 164 | 146 |
| 4 | Triethylamine | 1075 | 174 | 142 |
| 5 | Trimethylethylenediamine | 454 | 137 | 143 |

The data in Table 2 shows that the storage stability of these formulations are significantly improved upon the addition of amine to the catalyst composition. The composition without added amine (Example A) shows lack of curing after 285 hours of exposure to 65° C. Example 1 demonstrates that even small amounts of amine are effective to prolong the high-temperature storage life of these compositions.

EXAMPLE 6-7

To 1,670 parts of the catalyst composition of Preparatory Example 4 were added varying amounts of amine as indicated in Table 3. The amine and the catalyst composition of Preparatory Example 4 were mixed until homogeneous. As a comparison, Example B represents the catalyst composition of Preparatory Example 4 without added amine.

TABLE 3

| Example | Additive | (parts) | N:Pt ratio |
|---|---|---|---|
| B | None | 0.00 | 0.00 |
| 6 | PDMSDA[1] | 0.45 | 0.24 |
| 7 | PDMSDA | 4.07 | 2.10 |

[1]"PDMSDA" = a diamine having the approximate formula:

$$H_2NCH_2CH_2CH_2-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_{70}-\underset{\underset{CH_3}{|}}{\overset{\overset{CH_3}{|}}{Si}}-CH_2CH_2CH_2NH_2$$

Equal volumes of the amine containing catalyst composition and the crosslinker composition of Preparatory Example 5 (both compositions were viscous putties) were placed between two stainless steel rollers operating at 125 rpm for 20 seconds until mixed.

The silicone compound then begins to react (i.e., crosslink). Analysis of the setting time of the compositions was performed as described in Examples 1-5.

Listed below in Table 4 are the results of the "initial" setting time measurement for each sample (i.e., the setting time measured on a freshly prepared sample) and the setting time obtained after "aging" the sample at 65° C. for 359 to 672 hours.

TABLE 4

| Example | Additive | Aging Time (hours) | Setting Time Initial (secs.) | Setting Time Aged (secs.) |
|---|---|---|---|---|
| B | None | 359 | 187 | >600 |
| 6 | PDMSDA | 382 | 197 | 267 |
| 7 | PDMSDA | 672 | 196 | 253 |

The data in Table 4 shows that the storage stability of these formulations are significantly improved upon the addition of amine to the catalyst composition. The composition without added amine (Example B) shows lack of curing after 359 hours of exposure to 65° C. Example 6 demonstrates that even small amounts of amine are effective to prolong the high-temperature storage life of these compositions.

EXAMPLES 8-10

To 250 parts of the catalyst composition of Preparatory Example 6 were added varying amounts of amine or antioxidant as indicated in Table 5. As a comparison, Examples C and D represent the catalyst composition of Preparatory Example 6 with addition of an antioxidant in place of the amine. The amine or antioxidant and the catalyst composition of Preparatory Example 6 were mixed until homogeneous.

TABLE 5

| Example | Additive | (parts) | N:Pt ratio |
|---|---|---|---|
| C | BHT[1] | 0.064 | 0.00 |
| D | BHT | 0.19 | 0.00 |
| 8 | Triethylamine | 0.089 | 1.60 |
| 9 | Triethanolamine | 0.13 | 1.60 |
| 10 | Trimethylsilylpiperdine | 0.14 | 1.60 |

[1]"BHT" = Butyl hydroxy toluene.

Equal volumes of the amine or antioxidant containing catalyst composition and the crosslinker composition of Preparatory Example 7 were placed in separate barrels of a two-part syringe and tested as described in Examples 1-5.

Listed below in Table 6 are the results of the "initial" setting time measurement for each sample (i.e., the setting time measured on a freshly prepared sample) and the setting time obtained after "aging" the sample at 72° C. for 168 to 768 hours.

TABLE 6

| Example | Additive | Aging Time (hours) | Setting Time Initial (secs.) | Setting Time Aged (secs.) |
|---|---|---|---|---|
| C | BHT | 168 | 127 | 612 |
| D | BHT | 168 | 124 | >800 |
| 8 | Triethylamine | 768 | 137 | 91 |
| 9 | Triethanolamine | 768 | 160 | 106 |
| 10 | Trimethylsilyl-piperdine | 768 | 134 | 104 |

The data in Table 2 shows that the storage stability of these formulations are significantly improved upon the addition of amine to the catalyst composition. The compositions without added amine (Examples C and D) show degradation after 168 hours of exposure to 72° C.

EXAMPLE 11-13

To 2,500 parts of the catalyst composition of Preparatory Example 4 were added varying amounts of amine or antioxidant as indicated in Table 7. The amine or antioxidant and the catalyst composition of Preparatory Example 4 were mixed until homogeneous. As a comparison, Examples E and F represent the catalyst composition of Preparatory Example 4 with addition of an antioxidant in place of the amine.

TABLE 7

| Example | Additive | (parts) | N:Pt ratio |
|---|---|---|---|
| E | Vitamin E[1] | 0.16 | 0.00 |
| F | Irganox 1010[2] | 0.16 | 0.00 |
| 11 | Triethylamine | 0.07 | 0.64 |
| 12 | PDMSDA | 1.69 | 0.60 |
| 13 | PDMSDA | 3.48 | 1.20 |

[1]"Vitamin E" = tocopherol.
[2]"Irganox 1010" = a high molecular weight polyphenol stabilizer available from Ciba-Geigy Corp.

Equal volumes of the amine or antioxidant containing catalyst composition and the crosslinker composition of Preparatory Example 5 were tested as described in Examples 6-7.

Listed below in Table 8 are the results of the "initial" setting time measurement for each sample (i.e., the setting time measured on a freshly prepared sample) and the setting time obtained after "aging" the sample at 65° C. for 403 to 642 hours.

TABLE 8

| Example | Additive | Aging Time (hours) | Setting Time Initial (secs.) | Setting Time Aged (secs.) |
|---|---|---|---|---|
| E | Vitamin E | 403 | 273 | >600 |
| F | Irganox 1010 | 403 | 289 | >600 |
| 11 | Triethylamine | 430 | 260 | 264 |
| 12 | PDMSDA | 430 | 259 | 235 |
| 13 | PDMSDA | 642 | 269 | 246 |

The data in Table 8 shows that the storage stability of these formulations are significantly improved upon the addition of amine to the catalyst composition. The compositions without added amine (Examples E and F) shows lack of curing after 403 hours of exposure to 65° C.

We claim:
1. A composition comprising:
a curable silicone polymer,
a crosslinker,
a Karstedt platinum catalyst, wherein said Karstedt catalyst comprises a complex of a platinum halide and a complexing material in the form of an unsaturated organosilicon material, wherein said platinum-siloxane complex has available inorganic halogen of less than 0.1 gram atoms of halogen per gram atom of platinum, and
an effective amount of an amine stabilizer for increasing the storage stability of said catalyst, wherein said Karstedt catalyst and said amine stabilizer are provided in a first uncured part and said crosslinker is provided in a second uncured part that when combined with said first uncured part initiates the cure of said composition.

2. A composition according to claim 1, wherein said composition is capable of curing at a temperature of 32° C.

3. A composition according to claim 1, wherein said curable silicone polymer comprises at least one functional group capable of reacting with said crosslinker selected from the group consisting of vinyl, allyl, 1-hexenyl, and cyclohexenyl.

4. A composition according to claim 3, wherein at least one of said functional group is a vinyl group and is attached to said curable silicone polymer at a terminal site.

5. A composition according to claim 1, wherein said crosslinker comprises a compound having a silicon-hydrogen linkage.

6. A composition according to claim 5, wherein said compound having a silicon-hydrogen linkage is selected from the group consisting of organohydrogensilanes, organohydrogencyclopolysiloxanes, and organohydrogenpolysiloxanes.

7. A composition according to claim 1, wherein said crosslinker is selected from the group consisting of:
organohydrogensilanes having the empirical formula,

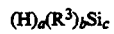

wherein each $R^3$ can be the same or different and represents an organic group, selected from the group consisting of monovalent hydrocarbyl groups, monovalent hydroalkoxyl groups and halogenated monovalent hydrocarbyl groups, c represents an integer having a value from 1 to 10,000, a represents an integer having a value at least 2 and less than or equal to c when c is greater than 1, and the sum of a and b equals the sum of 2 and two times c;

organohydrogencyclopolysiloxanes having the empirical formula, $$H_d R^3_e (SiO)_f$$

wherein $R^3$ is as defined above, f represents an integer having a value from 3 to 18, d represents an integer having a value at least 2 and less than or equal to f, and the sum of d and e equals two times f; and organohydrogenpolysiloxane polymers or copolymers having the empirical formula, $$(H)_g (R^3)_h Si_j O_{(j-1)}$$

wherein $R^3$ is as defined above, j represents an integer having a value from 2 to 10,000, g represents an integer having a value at least 2 and less than or equal to j, and the sum of g and h equals the sum of 2 and two times j.

8. A composition according to claim 1, wherein said platinum halide is selected from the group consisting of $H_2PtCl_6.nH_2O$, $NaHPtCl_6.nH_2O$, $KHPtCl_6.nH_2O$, $Na_2PtCl_6.nH_2O$, $K_2PtCl_6.nH_2O$, $PtCl_4.nH_2O$, $PtCl_2$, $Na_2PtCl_4.nH_2O$, $H_2PtCl_4.nH_2O$, $NaHPtCl_4.nH_2O$, $KHPtCl_4.nH_2O$, $K_2PtBr_4$, $[(CH_2=CH_2).PtCl_2]_2$, and $(PtCl_2.C_3H_6)_2$.

9. A composition according to claim 1, wherein said complexing material is selected from the group consisting of:

unsaturated silanes having the empirical formula, $$R_a R'_b Si_c X_z,$$

where R is free of aliphatic unsaturation and selected from monovalent hydrocarbon radicals, R' is selected from monovalent aliphatically unsaturated hydrocarbon radicals, X is a hydrolyzable radical, c is an integer having a value of between 1 and 10,000, b is an integer having a value greater than 2 and the sum of a, b and z equals the sum of 2 and two times c for a linear or branched silane and wherein c is an integer having a value from 4 to 18 and the sum of a, b and z equals two times c for a cyclic silane;

unsaturated linear or branched siloxanes of the formula, $$R_d R'_e Si_f O_{(f-1)},$$

where R and R' are as defined above, f is an integer having a value of between 2 and 10,000, e is an integer having a value greater than 2 and the sum of d and e equals the sum of 2 and two times f; and unsaturated cyclic siloxanes of the formula, $$R_d R'_e Si_f O_f,$$

where R and R' are as defined above, f is an integer having a value from 3 to 18, and the sum of d and e equals two times f.

10. A composition according to claim 1, wherein said complexing material contains at least one structural unit of the formula,

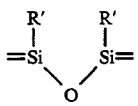

where the unsatisfied valences of the above structural unit can be satisfied by R, R' and oxygen radicals and where R is free of aliphatic unsaturation and selected from monovalent hydrocarbon radicals and R' is selected from monovalent aliphatically unsaturated hydrocarbon radicals.

11. A composition according to claim 1, wherein said amine stabilizer is selected from the group consisting of primary, secondary, and tertiary amines.

12. A composition according to claim 1, wherein said amine stabilizer is selected from the group consisting of propylamine, butylamine, pentylamine, hexylamine, dimethylamine, diethylamine, dipropylamine, di-n-butylamine, dipentylamine, trimethylamine, triethylamine, tripropylamine, tri-n-butylamine, tripentylamine, N-methyl diphenylamine, ethylene diamine, trimethylene diamine, tetramethylene diamine, pentamethylene diamine, hexamethylene diamine, aminopropyldimethyl terminated polydimethylsiloxane triethanolamine, piperidine, and trimethylsilylpiperdine.

13. A composition according to claim 1, wherein said amine stabilizer is selected from the group consisting of diamines, triamines, and tetraamines.

14. A composition according to claim 1, wherein said amine stabilizer further contains organopolysiloxane groups.

15. A composition according to claim 1, wherein said catalyst contains platinum and said amine stabilizer contains nitrogen and the ratio of nitrogen atoms to platinum atoms is greater than 0.05:1.

16. A composition according to claim 1, wherein said catalyst contains platinum and said amine stabilizer contains nitrogen and the ratio of nitrogen atoms to platinum atoms is between 0.2:1 and 10:1.

17. A composition according to claim 1, wherein said catalyst contains platinum and said amine stabilizer contains nitrogen and the ratio of nitrogen atoms to platinum atoms is between 0.8:1 and 4:1.

18. A composition according to claim 1, in the form of a dental impression comprising a negative mold of oral tissue.

19. A composition according to claim 1, in the form of a sealant, caulk, adhesive, coating, molding material, lithographic plate, release liner or reflective sheet.

20. A composition according to claim 1, wherein:
said curable silicone polymer comprises at least one vinyl functional group capable of reacting with said crosslinker and is attached to said curable silicone polymer at a terminal site and further comprises between 50 and 2000 siloxane groups;
said crosslinker is selected from the group consisting of organohydrogensilanes, organohydrogencyclopolysiloxanes, and organohydrogenpolysiloxanes and wherein said crosslinker contains Si-H groups and said polymer contains vinyl groups and the ratio of Si-H groups to vinyl groups is between 1:1 and 10:1;

said Karstedt platinum catalyst comprises a complex of a platinum halide and a complexing material in the form of an unsaturated organosilicon material and wherein said complexing material contains at least one structural unit of the formula,

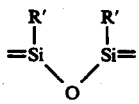

where the unsatisfied valences of the above structural unit can be satisfied by R, R' and oxygen radicals and where R is free of aliphatic unsaturation and selected from monovalent hydrocarbon radicals and R' is selected from monovalent aliphatically unsaturated hydrocarbon radicals; and said amine stabilizer is selected from the group consisting of primary, secondary, and tertiary amines.

21. A composition according to 20, wherein said amine stabilizer further contains organopolysiloxane groups.

22. A composition according to 20, wherein said catalyst contains platinum and said amine contains nitrogen and the ratio of nitrogen to platinum atoms is between 0.2:1 and 10:1.

23. A composition according to claim 1 further comprising fillers selected from the group consisting of pulverized metals, silica, quartz, calcium carbonate and metal oxides.

24. A composition according to claim 1, wherein said composition has a working time of greater than 2 minutes.

25. A composition according to claim 1, wherein said composition has a working time of greater than 0.5 minutes.

26. A composition according to claim 1, wherein said composition has a setting time of less than 10 minutes.

27. A composition according to claim 1, wherein said composition has a setting time of less than the sum of 5 minutes plus the working time.

28. A composition according to claim 1, wherein said composition's set time remains substantially unaffected by exposure to 50° C. temperatures for a period of 10 days.

29. A composition according to claim 1, wherein said composition's set time remains substantially unaffected by exposure to 65° C. temperatures for a period of 20 days.

* * * * *

UNITED STATES PATENT AND TRADEMARK OFFICE
CERTIFICATE OF CORRECTION

PATENT NO.: 5,371,162

DATED: December 6, 1994

INVENTOR(S): Mark S. Konings and Jeff P. Tane

It is certified that error appears in the above-identified patent and that said Letters Patent is hereby corrected as shown below:

Column 7, Lines 56-63, In diagram (F5) delete "$R_m^4$" and insert --$R^4_m$--

Column 9, Line 12, Delete "1-propynl" and insert -- 1-propynyl--.

Column 9, Line 43 & 44, insert a comma after tetraphenylcyclotetrasiloxane

Column 10, Line 17, Delete "37" and insert --"--

Signed and Sealed this

First Day of July, 1997

Attest:

BRUCE LEHMAN

*Attesting Officer*     *Commissioner of Patents and Trademarks*